United States Patent [19]

Schoeffel et al.

[11] 3,985,441

[45] Oct. 12, 1976

[54] MULTI-CHANNEL SPECTRAL ANALYZER FOR LIQUID CHROMATOGRAPHIC SEPARATIONS

[75] Inventors: Dietmar M. Schoeffel; Armin K. Sonnenschein, both of Hillsdale, N.J.

[73] Assignee: Schoeffel Instrument Corporation, Westwood, N.J.

[22] Filed: Mar. 13, 1974

[21] Appl. No.: 450,676

[52] U.S. Cl. .................................. 356/88; 356/95; 356/96; 356/97; 356/246
[51] Int. Cl.² ............................................ G01J 3/42
[58] Field of Search ............... 356/79, 82, 84, 85, 356/86, 88, 93–97

[56] References Cited
UNITED STATES PATENTS

| | | | |
|---|---|---|---|
| 2,823,577 | 2/1958 | Machler | 356/82 |
| 2,975,669 | 3/1961 | Jarrell et al. | 356/79 |
| 3,247,759 | 4/1966 | Saunderson | 356/86 X |
| 3,787,121 | 1/1974 | Lowry et al. | 356/97 X |
| 3,819,945 | 6/1974 | Egan et al. | 356/82 |

FOREIGN PATENTS OR APPLICATIONS

| | | | |
|---|---|---|---|
| 1,103,320 | 2/1968 | United Kingdom | 356/82 |

*Primary Examiner*—John K. Corbin
*Assistant Examiner*—F. L. Evans
*Attorney, Agent, or Firm*—Samuelson & Jacob

[57] ABSTRACT

Multi-channel analyzer for the optical comparison of sample fractions separated by liquid chromatography for detecting differences or ratios between, for example, reference and sample, solvent and sample, buffer and sample, or two different samples, having a single light source, a single dispersing element and a single collimating, refocusing optic for each spectrum produced, wherein the reference and sample passing through flow cuvettes are exposed and the ratio or difference between the optical characteristics of the reference and the sample are read.

5 Claims, 5 Drawing Figures

MULTI-CHANNEL SPECTRAL ANALYZER FOR LIQUID CHROMATOGRAPHIC SEPARATIONS

The invention relates to apparatus for measuring the optical characteristics of transparent or semitransparent substances in liquid or semiliquid form and in particular, to such apparatus which may make measurements in the field of high pressure, liquid chromatography, in which separations are accomplished with the utilization of columns.

Basic separations in liquid chromatography are produced by injecting the samples to be analyzed into a liquid stream above a separating column consisting of a tube-like container filled with adsorbents. The separation of these samples under investigation occurs due to capillary action and other phenomena well known in the modern practice of chromatography. Liquids, solvents, or buffers carry the samples through the column, and as media elutes from the exit of the column, the appearing solvents or buffers contain fractional components of materials of the originally injected substances. These fractions are optically detectable if their flow is directed through a flow-through cuvette, having an optical entrance and exit window which permits passage of a light beam. This light beam will change intensity when it is intercepted by passing fractions. Passing fractions, due to their characteristics, are indicated more or less by different spectral frequencies as is well known in the art of spectrophotometry.

In liquid chromatography fractions carried by solvent flow are, however, in the main very minute and exhibit only extremely small absorption or transmission changes, making their detection very difficult. The solvents or buffers used, as well as many of the compounds separated, are often of insufficient chemical stability over given time periods to be measurable on a reliable basis. As a consequence, certian nonrepeatable errors are present from one liquid chromatogram to another. It is therefore desirable to measure the characteristics of buffers or solvents at the same time as the characteristics of the separated materials are measured. A double beam approach, permitting the utilization of a reference and sample cuvette, has been found to be desirable. Since, as has been mentioned above, absorption or transmission changes in sample quantities as small as 5 microliters require accurate and practical presentation and since these absorption changes may amount to only a few ten thousandths of optical density (O.D.), long-term stability of the total system becomes a major objective in the solution of the measuring problem. It is therefore an object of the invention to provide such apparatus wherein the light utilized for measurement finds minimal impairment by optical or mechanical components and provides optical characteristics of similar nature in the reference and sample beams over long time periods. Since continuously adjustable UV and visible radiation is required to find most favorable absorption maximas for eluted media by the employment of monochromatic light produced by a dispersing element, such as, for example, a refraction grating, stability of the light source and uniformity of radiant flux impinging onto the cuvettes or flow cells become criteria of utmost importance.

To obtain and maintain the aforementioned stability, one of the objects of this invention is to obtain this uniformity and stability which is attainable with the conventional approaches used in the field of spectrophotometry which employ light sources, entrance slit illumination optics, monochromator with exit slits, exit radiation collimators, and rotating or modulating optical choppers to provide radiation for reference and sample measurements. In such conventional approaches, radiation emerging from the exit slits of monochromators having an elongated configuration, has to be condensed and optically treated to produce a fairly well collimated beam of a size suitable to pass through cuvettes with 1-mm aperture and 10-mm pathlength. This treatment of the beams exiting from the standard monochromator slits results in light loss and low energy passing through cuvettes with the effect that considerable amplification of the detector signals is necessary. This results in unstable and noisy signals and recording.

Since at least eight optical components are normally employed in conventional spectrophotometers of the double beam type and since these components consist of a condenser optic between the lamp and monochromator, a 45° reflector to reach the monochromator entrance slit, a major collimator in the monochromator (one if Littrow arrangements are used and two if Ebert arrangements are used), a dispersing element consisting of a prism or grating, a condenser and collimator optic after the exit slit of the monochromator, a beam splitter or chopper arrangement consisting normally of two standing and two chopping or oscillating mirrors (of the latter, one standing and one chopping mirror exclusively serves for the reference and one pair of similar ones serves for the sample channel to reach reference and sample cuvettes alternately), a great number of unlike surface areas and areas of possible mechanical instability, which make detection of minute differences between samples and references extremely difficult, are introduced. As a consequence, a certain error is present in all existing monochromatic readout systems unless steps are taken to minimize the optical inconsistencies and mechanical instabilities. A further object of the present invention is to provide apparatus which will eliminate the systems errors and reduce the number of optical components used for the production of two identical spectra to illuminate reference and sample to a minumum of three, and to replace choppers utilizing rotating or oscillating optical surfaces for the purpose of dividing radiation into reference and sample beams by two individual detectors or by a nonoptical reciprocating vane and signal gating for maximum readout stability.

A still further object of the invention is to utilize a similar or the same portion of the flux envelope emitted by a light source and to focus the original source point of the light source in a dispersed manner in the form of two defined identical spectra produced via one reflection-type diffraction grating or refraction-type dispersing optic onto two similar cuvettes or onto the unknown sample and reference areas. This is accomplished by refocusing the light source either with a multi-directional spherical or aspherical, corrected, refocusing, reflection, mirror-type optic which is ground, polished, and coated with a reflection surface or by refocusing by means of a multi-directional transmission optic which reproduces two identical spectrally dispersed images of the light source in the plane of the reference and sample cuvette or on the reference or the sample area, after being reflected and refracted by a reflection-type diffraction grating or refraction-type dispersion optic.

By using the approach described above, possible light source energy fluctuations, resulting in higher and lower radiant flux over short or long durations, are equally expressed in the reference and sample beam. It is therefore also an object of the invention to have light source fluctuations transferred into separate sample and reference areas via only one dispersion and one multi-directional refocusing optic for instantaneous photoelectric comparison and formation of ratios between sample and reference energy with a resulting ratio of 1 for the electrical expression of a reliable zero for measuring purposes, since the energies of the sample and reference will be almost identical.

This can also be expressed as follows. Light intercepted from the radiant flux emitting area of the light source reaches two areas after dispersion of two directional beams by one dispersing element. The two areas contain the same energy. This energy can, however, differ in intensity due to reduced flux over the lifetime of the source and due to deterioration of the optical surfaces. Since identical areas of reflecting and/or transmitting optics and the same area of a dispersion or refraction optic are used, the reduction of energy will be equally expressed and the ratio of energy between the sample and reference beam will be one to one if these beams are unimpaired by energy-reducing or energy-adding substances, such as absorbing or flourescing substances, regardless of the energy level emitted by the light source or impaired by optical effects. As an example, assume that the sample beam contains radiation to produce a photoelectric signal of 5 V and the reference beam contains radiation to produce 5 V at the beginning of a long-term test. The ratio of 5 V over 5 V equals 1. As the test proceeds, the light output of the source and the dispersion and multi-directional refocusing optic deteriorates to yield only 2 V in the sample beam and 2 V in the reference beam. The resulting ratio of 2 V over 2 V equals 1. If the ratio of 1 is utilized to provide a readout of transmission, the transmission of energy through an empty sample cuvette will always be 100 percent of the energy available through the empty reference cuvette or the optical density of the empty sample cuvette will be zero before introduction of the sample to be measured, regardless of actual light energy level emitted by the source or transmitted by the system.

It is a still further object of the invention to provide apparatus wherein an aperture within the light source or directly in front of the source, limiting the size of such source, is refocused in the same manner into the plane of the sample and reference beam by the same multi-directional refocusing optic and only one dispersing element.

It is yet another object of the invention to provide a single reflecting condensing and refocusing optic after the plane of reference and sample cuvette mounting to intercept energy emerging from such sample and reference cuvettes and to refocus such energies by means of demagnification into an area of extreme proximity onto a single photodetection element.

It is still a further object of the invention to employ two like sections of the same reflecting element after the sample and reference cuvettes to recombine and superimpose true images of the aperture, limiting the light source size.

It is still another object of the invention to utilize the light energy emerging from similar spectral areas of the spectra displayed in the sample and reference plane to illuminate flourescent and refraction-type cuvettes for photoelectric determination of flourescence or refractive index changes in the measured media via the same apertures.

And it is still another object of the invention to provide light access to the readout photodetector in an alternating mode for reference and sample ratio determination via a reciprocating nonoptical shutter vane driven by a unique stepper drive.

It is also one of the objects of the invention to utilize the stepper drive and its characteristics for alternate signal interception and to overcome conventional instabilities and nonreproducibilities caused by mechanical imperfections, temperature dependencies of motor-magnets and coils via exactly timed electronic gating of the signals, eliminating the leading and trailing slopes, only utilizing the flat portion of the sample and reference signal.

These and other objects, advantages, features, and uses will be apparent during the course of the following description when taken in conjunction with the accompanying drawing wherein.

Figure 1:
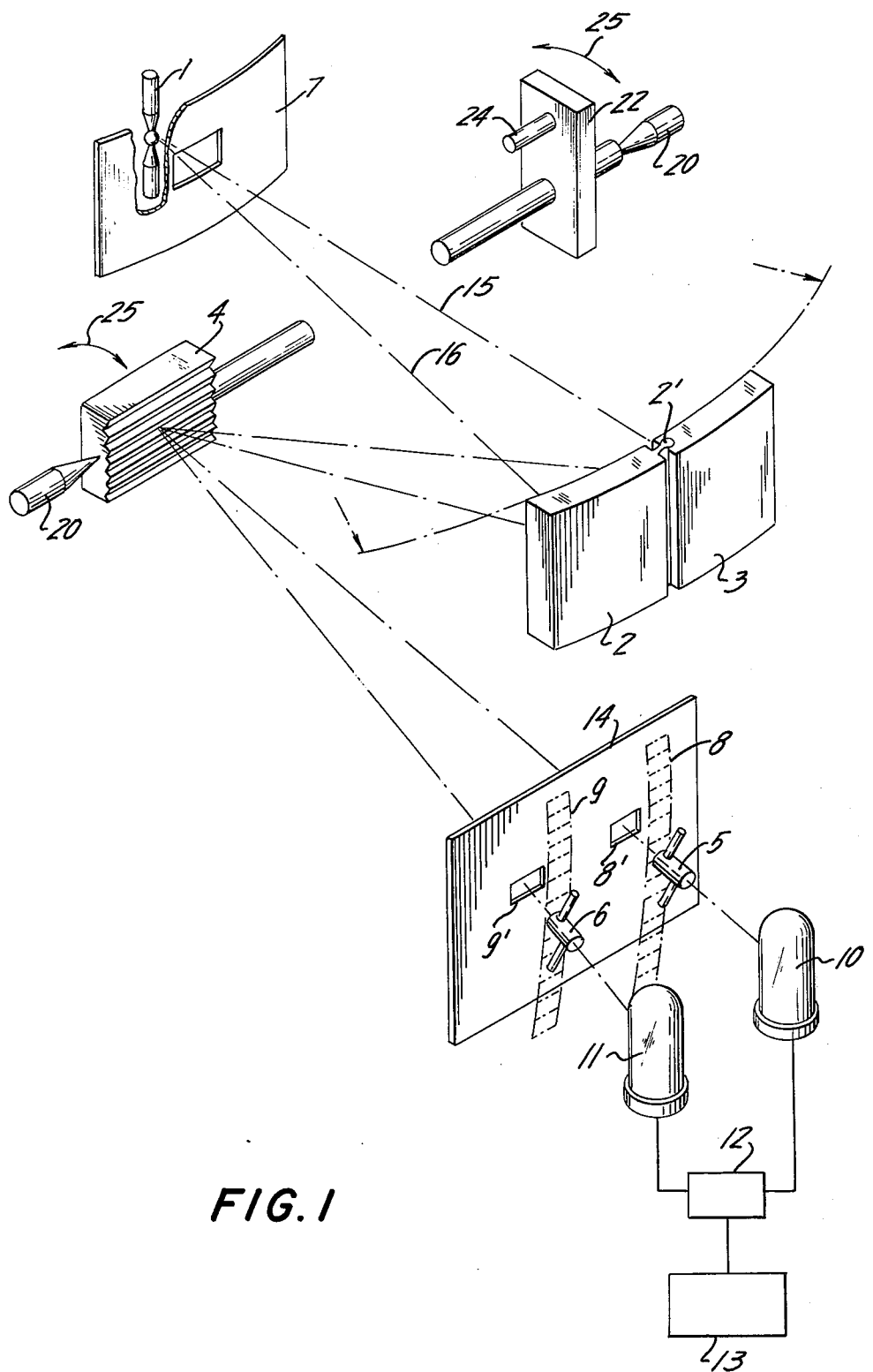
FIG. 1 is an exploded view, in perspective, of an embodiment of the invention.

In the drawing, wherein, for the purpose of illustration, are shown preferred embodiments of the invention, and wherein like numerals designate like parts throughout the same, the numeral 1 designates a source of light (FIG. 1). This source of light is depicted as an arc source which radiates through a full circle of 360°. Since the full circle of radiation cannot be intercepted by optics, a slit mask 7 is mounted as closely as possible to the arc source to provide only illumination to the multi-directional refocusing optic which consists of components 2 and 3.

This multi-directional refocusing optic as depicted features a hinge connection 2' to provide accurate grinding and polishing and to produce identical radii for components 2 and 3. After overcoating of the polished surfaces with reflecting material, reflection surfaces are produced which permit one to illuminate an identical area on a grating 4 by either portion of the multi-directional refocusing optics 2 and 3. The light reaching the grating 4 is dispersed by this grating into spectra 8 and 9. Light reaching the area of the projected spectra is restricted by aperture plate 14 which contains two identical apertures 8' and 9' to permit only selected portions of the spectra to reach the flow-through or spectrophotometric cuvettes 5 and 6. Light passing through cuvettes 5 and 6 then reaches photodetectors 10 and 11 which are connected to ratio circuitry 12 to compare the signals by producing ratios thereof for display or readout recorders or readout 13. The grating 4 can be tilted between pivot points 20 by arm 22 through an angle indicated by the arrows 25 using a follower pin 24 and a standard sine drive as is well known in the construction of monochromators and whose details are not depicted herein. The change of angle of grating 4 accomplishes the sweeping of spectra 9 and 8 across the apertures 8' and 9'. If grating 4 is moved in an angular fashion as indicated by directional arrow 25, two identical spectra, produced by the same area of the grating and originating from the same apex of the central rays originating from the source and directed toward the grating by multi-directional refocusing optic 2 and 3, will sweep across the two apertures 8' and 9' in aperture plate 14 for selection of desired spectral areas to illuminate cuvettes 5 and 6.

FIG. depicts a sysyem very similar to that described and shown in FIG. 1 with two added components in the multi-directional refocusing optic designated 35 and 36. The addition of these two components having similar surfaces to those of components 2 and 3 permits one to illuminate a single grating with two additional light beams reaching the same apex point on grating 4 and being dispersed by grating 4 into two additional spectra 43 and 44 apertured by apertures 43' and 44' on aperture plate 14. The two additional spectra reach photodetectors 41 and 42. The addition of these two photodetectors depicts clearly one of the advantages of the invention to produce several identical spectra in at least pairs of two as designated by numerals 8 and 9 or 43 and 44 to provide a spectrophotometric apparatus which contains only one grating but provides several analyzing channels without employment of beam-dividing choppers and originating from one radiating source. As clearly shown, cuvettes 5, 6, 39, and 40 can be utilized for spectrophotometric measurements and comparison by the usual ratio circuitry and readout.

Figure 3:
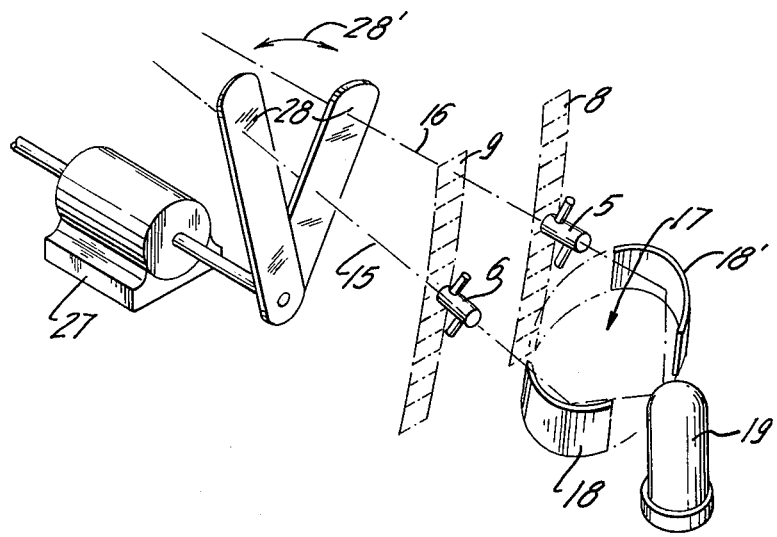
FIG. 3 is an exploded view, in perspective, of a still further embodiment of the invention depicting a single reflecting condensing and refocusing optic and sections thereof for energy interception and depicting a nonoptical shutter vane on a reciprocating electromechanical drive.

FIG. 3 depicts a configuration of the apparatus in which two channels, used to determine ratios between sample and reference, can be served by one single photodetector 19 by using an elliptical or other aspherical beam combiner optic 17 or sections thereof as shown and designated with numerals 18 and 18'. In this configuration beams 15 and 16, constituting the central beams of spectra 8 and 9 reaching the cuvettes 5 and 6, are alternately permitted by chopper blade 28 to reach photomultiplier 19. Chopper blade 28 is driven by motor 27 in a reciprocating motion as shown by arrows 28'.

Figure 2:
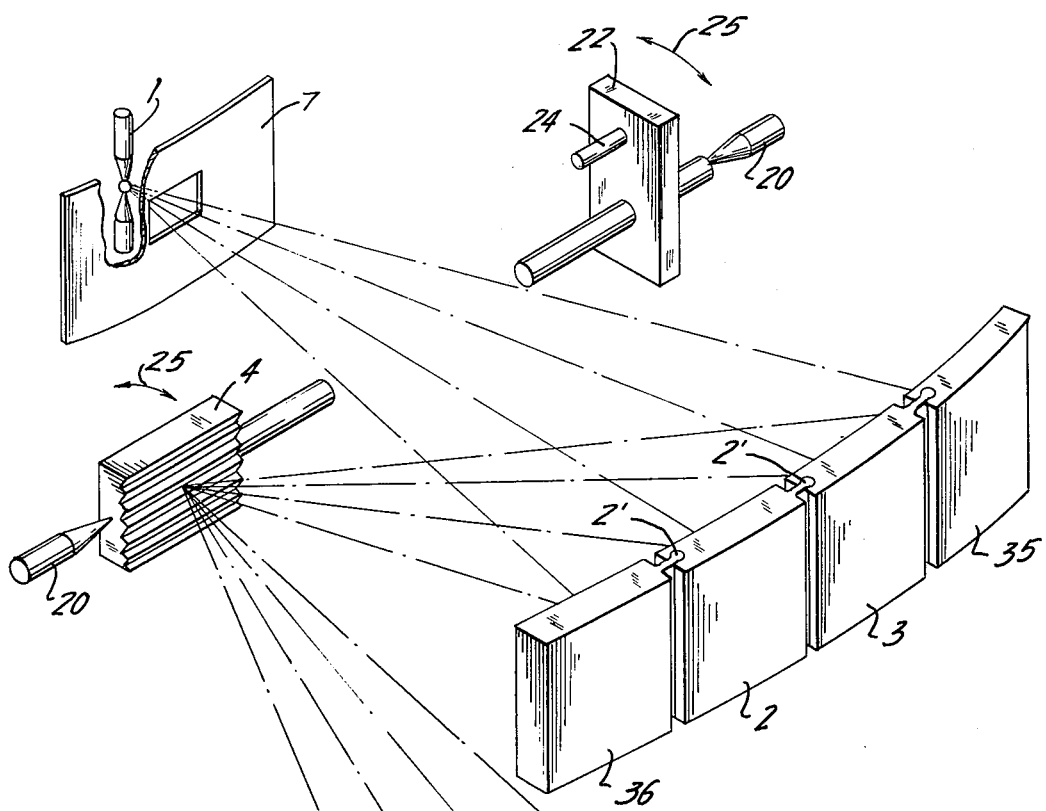
FIG. 2 is an exploded view, in perspective, of a further embodiment of the invention depicting a duplication of the reference and sample arrangement resulting in two reference and two sample beams.
Figure 2:
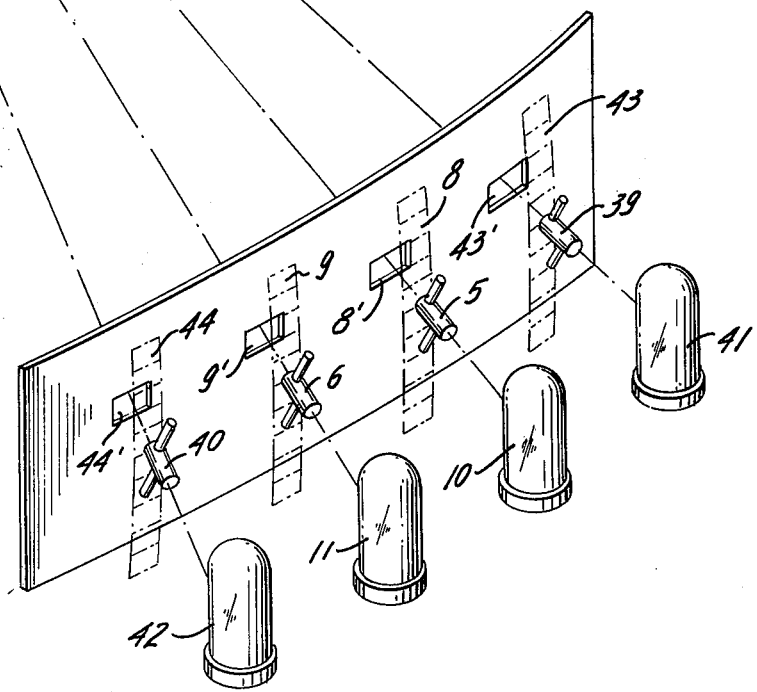

It is also within the scope of the invention to use two such choppers or one with two reciprocating blades and two photodetectors with the four channel construction of FIG. 2.

Figure 4:
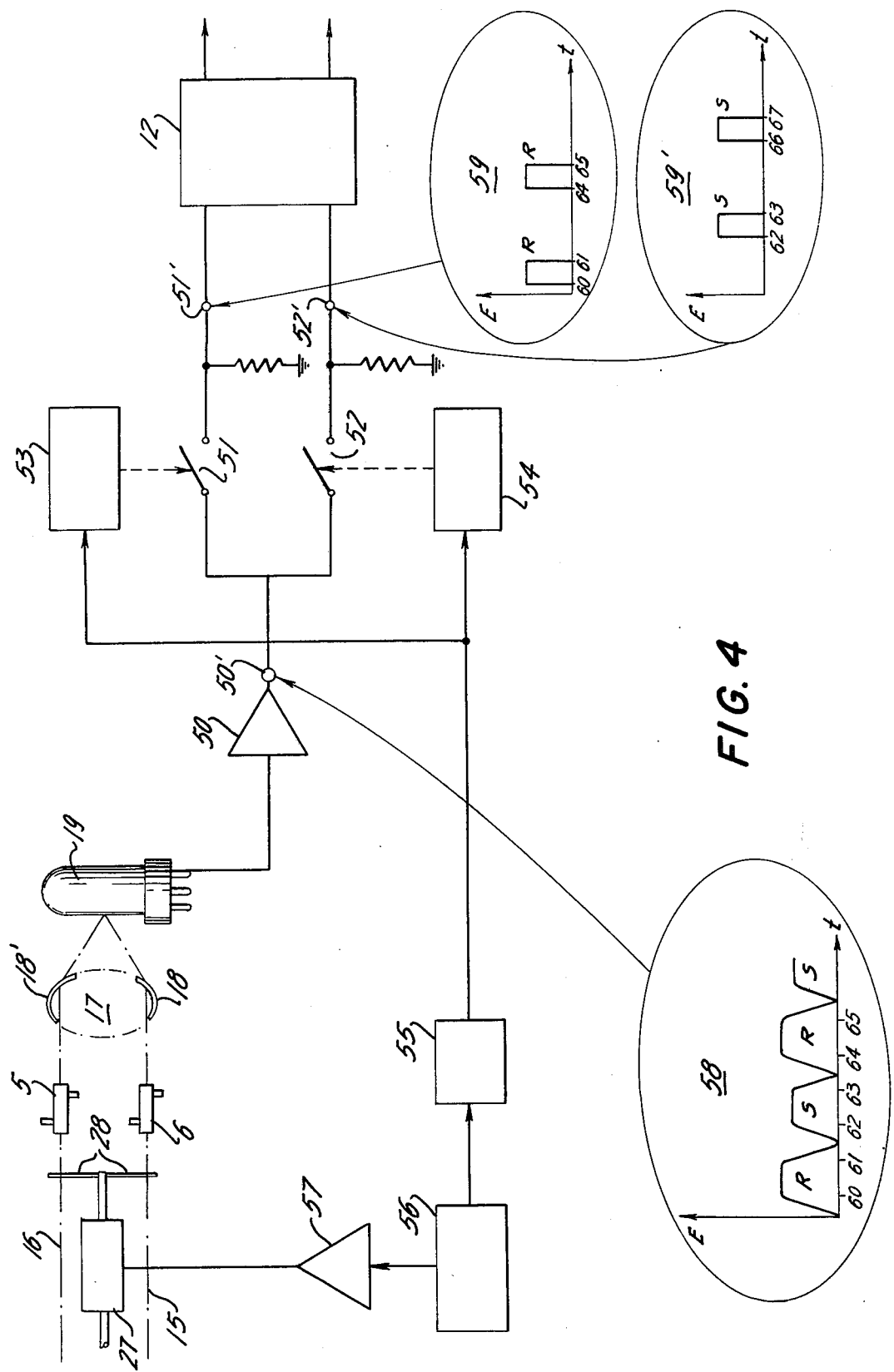
FIG. 4 is a functional block diagram showing the principal electronic elements for driving the stepping motor and the precision gating electronics as well as the signal versus time graphs at selected points in the circuit.

FIG. 4 shows a sine wave generator 56 and driver amplifier 57 for controlling the stepping or chopper motor 27 and chopper blade 28 to move one step in a clockwise direction during the positive half wave to permit beam 16 to pass and one step in counterclockwise direction to permit beam 15 to pass during the negative half wave. The detector 19 therefore sees the signal obtained with the light beam 16 passing through cuvette 6 which is marked as sample signal S in the graphs 58 and 59' which depict the signals appearing at points 50' and 52', respectively. Since the inertia of stepping motor 27 causes a time delay or a phase shift, the phase shifter 55 delays or shifts the phase of the sine wave generated by 56 by the same amount as the stepping motor delays its mechanical action. The shifted sine wave at the output of phase shift 55 produces an accurately timed pulse by means of the pulse generator 53 during the positive half wave. The pulse generator 54 generates an accurately timed pulse during the negative half wave. These pulses drive solid state switches 51 and 52 in a manner such that the signal wave from photodetector 19, which has been amplified by amplifier 50, and as shown in graph 58, is conducted only during the plateau portion of the signal R and S. The signal of graph 58 is at the same time separated into two signals which are shown in graphs 59 and 59'. Graph 59 appears at point 51'. One signal channel contains only R signals, and other signal channel contains only S signals. The ON time of the drive pulses from generators 53 and 54 is identical, therefore, the integrated area of the pulse R in graph 59 represents the reference signal R, and the integrated area of the pulse S in graph 59' represents the sample signal S, eliminating the influence of the uncertainty of the leading and trailing slopes of the signals R and S as shown in graph 58. The switching points of the switches 51 and 52 are marked with the same numbers in graphs 58 and 59 and 59' to show which portion of the wave of graph 58 has been transferred by the switches 51 and 52 as shown in graphs 59 and 59'. Ratio circuitry 12 contains ratio electronics with outputs to feed readout devices well known in the art.

Figure 5:
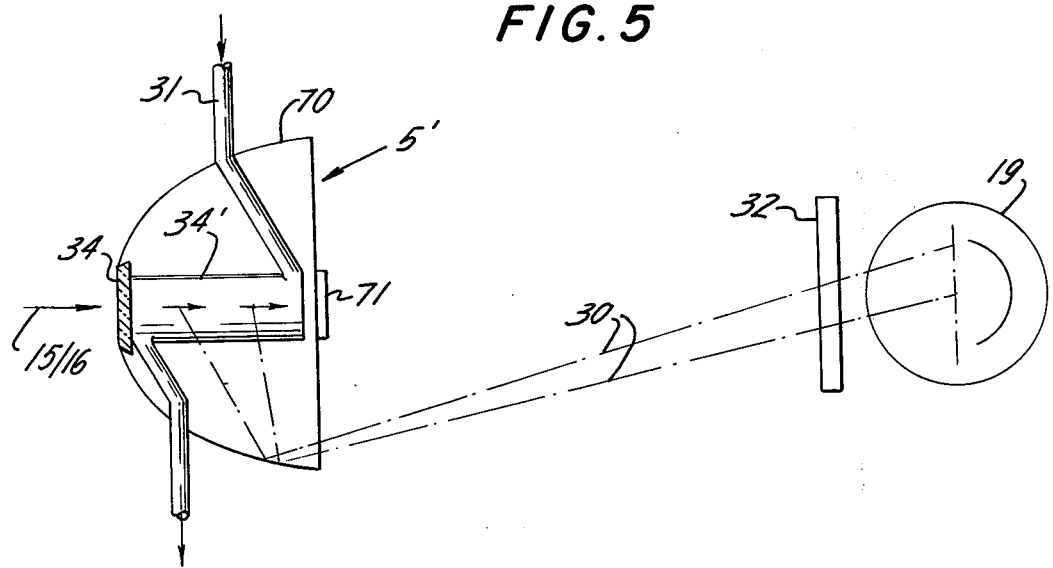
FIG. 5 (on the same sheet as FIG. 3) is an elevational view, partly in section, of a flow-through cuvette used in the apparatus of the invention for flourescence detection.

FIG. 5 is a view of a special version of a cuvette 5' for flourescence investigation using the apparatus of the invention, in which the body of cuvette 5' is formed of quartz or other suitable material through which a liquid flow for detection and analysis is directed. This cuvette 5' is embedded in a clear plastic or glass block 70 having a spherical, aspherical, or elliptical configuration or surrounded by an elliptical, spherical, or aspherical reflector to direct flourescence emerging from the walls of cuvette 5' to photodetector 19 through a filter 32. The propagation of rays, indicated as dotted lines, is designated by the numeral 30. The cuvette 5' operates by exiciting the spectral energy, originating out of beam 15 or 16, as illustrated in FIG. 1, through window 34. Flourescence samples, which have entered through port 31 and are present in the main body portion 34' of cuvette body 5', are excited by this entering radiation which cannot exit and reach photodetector 19 directly due to mask 71, will radiate and this radiant energy will be reflected as described before.

While particular embodiments of the invention have been shown and described, it is apparent to those skilled in the art that modifications are possible without departing from the spirit of the invention or the scope of the subjoined claims.

The embodiments of the invention in which are exclusive property or privelege is claimed are defined as follows:

1. A multi-channel analyzer for liquid chromatographic separations for comparing at least two liquids such as a reference and an unknown sample comprising:
   a single light source;
   an optical grating;
   reflection means for directing a plurality of beams from the single light source to an identical area of the optical grating, the plurality of beams being spaced from one another such that the beams will establish identical spectra emanating from the identical area of the optical grating, the identical spectra being spaced from one another;

a plurality of spaced aperture means for permitting selected portions of the spectra to pass therethrough;

a plurality of containing means for containing the liquids being analyzed, there being an aperture means associated with each containing means;

detecting means for separately detecting the light passing through each containing means of the plurality of containing means;

comparison means for comparing the several signals detected by the detecting means.

2. The invention of claim 1 wherein there are two spaced aperture means and two detecting means, there being a detecting means associated with each aperture means.

3. The invention of claim 1 wherein there are four aperture means and four detecting means, there being a detecting means associated with each aperture means.

4. The invention of claim 1 wherein there are two aperture means, namely, first aperture means and second aperture means and a single detecting means and including:

an opaque blade;

moving means for moving the opaque blade between a first position in which the light directed toward the first aperture means passes through the said first aperture means and the light directed toward the second aperture means is precluded from reaching the said second aperture means and a second position in which the light directed toward the second aperture means passes through the said second aperture means and the light directed toward the first aperture means is precluded from reaching the said first aperture means; and focusing means for directing the beams passing through the apertures to the single detecting means.

5. The invention of claim 4 wherein:

there are two sets of two aperture means, two detecting means, two opaque blades, two moving means and two focusing means;

there being one opaque blade and one focusing means associated with two aperture means and one detecting means.

* * * * *